United States Patent

Brooks et al.

[11] Patent Number: 5,506,261
[45] Date of Patent: Apr. 9, 1996

[54] SUBSTITUTED ARYL- AND HETEROARYLALKENYL-N-HYDROXYUREA INHIBITORS OF LEUKOTRIENE BIOSYNTHESIS

[75] Inventors: Dee W. Brooks; Andrew O. Stewart, both of Libertyville, Ill.; Richard A. Craig, Racine, Wis.

[73] Assignee: Abbott Laboratories, Abbott Park, Ill.

[21] Appl. No.: 239,648

[22] Filed: May 9, 1994

[51] Int. Cl.$^6$ .................... C07D 333/32; C07D 333/34; A61K 31/38; A61K 31/385

[52] U.S. Cl. ............... 514/438; 514/445; 549/62; 549/65

[58] Field of Search ............ 549/62, 65; 514/438, 514/445

[56] References Cited

U.S. PATENT DOCUMENTS 5,169,854 12/1992 Brooks et al. .................. 514/314
5,288,751 2/1994 Brooks et al. .................. 514/438

FOREIGN PATENT DOCUMENTS 320628 6/1989 European Pat. Off. ...... C07D 207/32
WO90/12008 10/1990 WIPO .................. C07C 275/64

Primary Examiner—Alan L. Rotman
Attorney, Agent, or Firm—Jerry F. Janssen

[57] ABSTRACT

Compounds of the structure

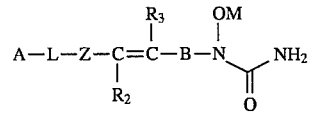

wherein Z is selected from optionally substituted thienyl, thiazolyl, oxazolyl and furyl are potent inhibitors of lipoxygenase enzymes and thus inhibit the biosynthesis of leukotrienes. These compounds are useful in the treatment or amelioration of allergic and inflammatory disease states.

7 Claims, No Drawings

SUBSTITUTED ARYL- AND HETEROARYLALKENYL-N-HYDROXYUREA INHIBITORS OF LEUKOTRIENE BIOSYNTHESIS

TECHNICAL FIELD

This invention relates to compounds having activity to inhibit leukotriene biosynthesis, to pharmaceutical compositions comprising these compounds, and to a medical method of treatment. More particularly, this invention concerns certain substituted aryl- and heteroaryl-alkenyl-N-hydroxyureas which inhibit leukotriene biosynthesis, to pharmaceutical compositions comprising these compounds and to a method of inhibiting 5-lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis- 2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

U.S. Pat. No. 4,738,986 to Kneen, et al. discloses and claims N-(3-phenoxycinnamyl)acetohydroxamic acid, its salts and related compounds having utility for inhibiting lipoxygenase and cyclooxygenase enzymes.

European Patent Application 299 761 to Salmon, et al. discloses and claims certain (substituted phenoxy)phenylalkenyl hydroxamic acids and their salts which are useful as agents for inhibiting lipoxygenase and cyclooxygenase activity.

European Patent Application Serial No. 93 904 979.7 filed Feb. 8, 1993 to Brooks, et al. discloses and claims certain (substituted furanylalkenyl-N-hydroxyureas and hydroxamic acids having lipoxygenase inhibiting activity.

SUMMARY OF THE INVENTION

In its principal embodiment, the present invention provides certain substituted aryl- and heteroaryl-alkenyl-N-hydroxyurea compounds which inhibit 5-lipoxygenase enzyme activity and are useful in the treatment of allergic and inflammatory disease states in which leukotrienes play a role including including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The present invention provides a compound of formula

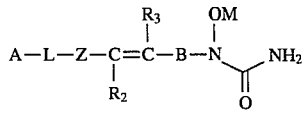

or a pharmaceutically acceptable salt thereof in which $R_2$ and $R_3$ are independently selected from hydrogen, alkyl of one to twelve carbon atoms, halogen and trifluoromethyl. M represents hydrogen, a pharmaceutically acceptable cation, or a pharmaceutically acceptable metabolically cleavable group; B is a straight or branched divalent alkylene group of one to twelve carbon atoms; and L is alkylene of one to six carbon atoms.

Z is selected from (a) thienyl, optionally substituted with alkyl of one to six carbon atoms, or haloalkyl of one to six carbon atoms; (b) thiazolyl, optionally substituted with alkyl of one to six carbon atoms or haloalkyl of one to six carbon atoms, (c) oxazolyl, optionally substituted with alkyl of one to six carbon atoms or haloalkyl of one to six carbon atoms, and (d) furanyl, optionally substituted with alkyl of one to six carbon atoms or haloalkyl of one to six carbon atoms.

A is selected from (a) optionally substituted phenyl, (b) optionally substituted naphthyl, where the optional substituents on the phenyl or naphthyl groups are selected from the group consisting of (1) alkyl of one to six carbon atoms, (2) haloalkyl of one to six carbon atoms, (3) hydroxyalkyl of one to six carbon atoms, (4) alkoxy of one to twelve carbon atoms, (5) alkoxyalkoxyl in which the two alkoxy portions may each independently contain one to six carbon atoms, (6) alkylthio of one to six carbon atoms, (7) hydroxy, (8) halogen, (9) cyano, (10) amino, (11) alkylamino of one to six carbon atoms, (12) dialkylamino in which the two alkyl groups may independently contain one to six carbon atoms, (12) alkanoylamino of two to eight carbon atoms, (13) N-alkanoyl-N-alkylamino in which the alkanoyl portion may contain from two to eight carbon atoms and the alkyl groups may each independently contain one to six carbon atoms, (14) alkylaminocarbonyl of two to eight carbon atoms, (15) dialkylaminocarbonyl in which the two alkyl groups may independently contain one to six carbon atoms,

(16) carboxyl, (17) alkoxycarbonyl of two to eight carbon atoms, (18) phenyl, optionally substituted with alkyl of one to six carbon atoms, haloalkyl of one to six carbon atoms, alkoxy of one to six carbon atoms, hydroxy, or halogen, (19) phenoxy, optionally substituted with alkyl of one to six carbon atoms, haloalkyl of one to six carbon atoms, alkoxy of one to six carbon atoms, hydroxy, or halogen, (20) phenylthio, optionally substituted with alkyl of one to six carbon atoms, haloalkyl of one to six carbon atoms, alkoxy of one to six carbon atoms, hydroxy, or halogen, (21) pyridyl, optionally substituted with alkyl of one to six carbon atoms, haloalkyl of one to six carbon atoms, alkoxy of one to six carbon atoms, hydroxy, halogen, or phenyl optionally substituted with alkyl or halogen, (22) pyridyloxy, optionally substituted alkyl of one to six carbon atoms, haloalkyl of one to six carbon atoms, alkoxy of one to six carbon atoms, hydroxy, or halogen; (c) optionally substituted furyl, where the optional substituents are selected from (c-1) alkyl of one to six carbon atoms, (c-2) haloalkyl of one to six carbon atoms, (c-3) halogen, (c-4) phenyl, optionally substituted with alkyl of one to six carbon atoms, haloalkyl of one to six carbon atoms, alkoxy of one to six carbon atoms, hydroxy, or halogen, (c-5) phenoxy, optionally substituted with alkyl of one to six carbon atoms, haloalkyl of one to six carbon atoms, alkoxy of one to six carbon atoms, hydroxy, or halogen, (c-6) phenylthio, optionally substituted with alkyl of one to six carbon atoms, haloalkyl of one to six carbon atoms, alkoxy of one to six carbon atoms, hydroxy, or halogen, (c-7) pyridyl, optionally substituted with alkyl of one to six carbon atoms, haloalkyl of one to six carbon atoms, alkoxy of one to six carbon atoms, hydroxy, or halogen, and (c-8) pyridyloxy, optionally substituted with alkyl of one to six carbon atoms, haloalkyl of one to six carbon atoms, alkoxy of one to six carbon atoms, hydroxy, or halogen; (d) optionally substituted thienyl, where the optional substituents are selected from the group consisting of (d-1) alkyl of one to six carbon atoms, (d-2) phenyl, optionally substituted with alkyl of one to six carbon atoms, haloalkyl of one to six carbon atoms, alkoxy of one to six carbon atoms, hydroxy, or halogen, (d-3) phenoxy, optionally substituted with alkyl of one to six carbon atoms, haloalkyl of one to six carbon atoms, alkoxy of one to six carbon atoms, hydroxy, or halogen, (d-4) phenylthio, optionally substituted with alkyl of one to six carbon atoms, haloalkyl of one to six carbon atoms, alkoxy of one to six carbon atoms, hydroxy, or halogen, (d- 5) pyridyl, optionally substituted with alkyl of one to six carbon atoms, haloalkyl of one to six carbon atoms, alkoxy of one to six carbon atoms, hydroxy, or halogen, and (d-6) pyridyloxy, optionally substituted with alkyl of one to six carbon atoms, haloalkyl of one to six carbon atoms, alkoxy of one to six carbon atoms, hydroxy, or halogen; (e) optionally substituted benzo[b]furyl; (f) optionally substituted benzo[b]thienyl; (g) optionally substituted pyridyl; and (h) optionally substituted quinolyl, where the optional substituents on the benzo[b]furyl, benzo[b]thienyl, pyridyl, and quinolyl groups are selected from alkyl of one to six carbon atoms, haloalkyl of one to six carbon atoms, alkoxy of one to six carbon atoms, hydroxy, and halogen.

In another embodiment, the present invention provides pharmaceutical compositions which comprise a therapeutically effective amount of compound as defined above in combination with a pharmaceutically acceptable carrier.

In yet another embodiment, the present invention provides a method of inhibiting leukotriene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the structure —NHR' wherein R' is alkyl, as previously defined, Examples of alkylamino include methylamino, ethylamino, iso-propylamino and the like.

The term "alkylaminocarbonyl" refers to an alkylamino group, as previously defined, attached to the parent molecular moiety through a carbonyl, >C=O, group. Examples of alkylaminocarbonyl include methylaminocarbonyl, ethylaminocarbonyl, iso-propylaminocarbonyl and the like.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkanoyl" represents an alkyl group, as defined above, attached to the parent molecular moiety through a carbonyl group. Alkanoyl groups are exemplified by acetyl, propionyl, butanoyl and the like.

The term "alkanoylamino" refers to an alkanoyl group, as previously defined, attached to the parent molecular moiety through a nitrogen atom. Examples of alkanoylamino include formamido, acetamido, and the like.

The term "N-alkanoyl-N-alkylamino" refers to an alkanoyl group, as previously defined, attached to the parent molecular moiety through an aminoalkyl group. Examples of N-alkanoyl-N-alkylamino include N-methyl-formamido, N-methyl-acetamido, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkoxyl) refers to an alkyl group, as defined above, attached through an oxygen to an alkyl group, as defined above, attached through an oxygen to the parent molecular moiety. Examples of alkoxyalkoxyl include methoxymethoxyl, methoxyethyoxyl, ethoxyethoxyl and the like.

The term "alkoxyalkyl" refers to an alkoxy group, as defined above, attached through an alkylene group to the parent molecular moiety.

The term "alkoxycarbonyl" represents an ester group; i.e. an alkoxy group, attached to the parent molecular moiety through a carbonyl group such as methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl- 2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH₂CH=CH—, —C(CH₃)=CH—, —CH₂CH=CHCH₂—, and the like.

The term "alkynylene" refers to a divalent group derived by the removal of two hydrogen atoms from a straight or branched chain acyclic hydrocarbon group containing a carbon-carbon triple bond. Examples of alkynylene include —CH∫CH—, —CH∫C—CH₂—, —CH∫CH—CH(CH₃)— and the like.

The term "carbocyclic aryl" denotes a monovalent carbocyclic ring group derived by the removal of a single hydrogen atom from a monocyclic or bicyclic fused or non-fused ring system obeying the "4n+2 p electron" or Huckel aromaticity rule. Examples of carbocyclic aryl groups include phenyl, 1- and 2-naphthyl, biphenylyl and the like.

The term "(carbocyclic aryl)alkyl" refers to a carbocyclic ring group as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moeity through a sulfur atom and thence through an alklyene group and are typified by phenylthiomethyl, 1- and 2-naphthylthioethyl and the like.

The term "dialkylamino" refers to a group having the structure —NR'R" wherein R' and R" are independently selected from alkyl, as previously defined. Additionally, R' and R" taken together may optionally be —(CH₂)$_{kk}$— where kk is an integer of from 2 to 6. Examples of dialkylamino include, dimethylamino, diethylaminocarbonyl, methylethylamino, piperidino, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "phenoxy" refers to a phenyl group attached to the parent molecular moiety through an oxygen atom.

The term "phenylthio" refers to a phenyl group attached to the parent molecular moiety through a sulfur atom.

The term "pyridyloxy" refers to a pyridyl group attached to the parent molecular moiety through an oxygen atom.

The term "metabolically cleavable group" denotes a group which is cleaved in vivo to yield the parent molecule of the structural formulae indicated above wherin M is hydrogen. Examples of metabolically cleavable groups include —COR, —COOR, —CONRR and —CH₂OR radicals where R is selected independently at each occurrence from alkyl, trialkylsilyl, carbocyclic aryl or carbocyclic aryl substituted with one or more of $C_1$-$C_4$ alkyl, halogen, hydroxy or $C_1$-$C_4$ alkoxy. Specific examples of representative metabolically cleavable groups include acetyl, methoxycarbonyl, benzoyl, methoxymethyl and trimethylsilyl groups.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences,* 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Asymmetric centers may exist in the compounds of the present invention. The present invention contemplates the various stereoisomers and mixtures thereof. Starting compounds of particular stereochemistry are either commercially available or are made by the methods detailed below and resolved by techniques well known in the organic chemical arts.

Compounds falling within the scope of the present invention include, but are not limited to:

Z-(R)-N-[3-(5-(4-Fluorophenylmethyl)-thien-2-yl)-1-methyl-2-propenyl]-N-hydroxyurea, E-(R)-N-[3-(5-(4-Fluorophenylmethyl)-thien-2-yl)-1 -methyl-2-propenyl]-N-hydroxyurea, Z-N-[3-(5-(4-Fluorophenylmethyl)-thien-2-yl)-1-methyl-2-propenyl]-N-hydroxyurea, E-N-[3-(5-(4-Fluorophenylmethyl)-thien-2-yl)-1-methyl-2-propenyl]-N-hydroxyurea, Z-N-[3-(5-(4-Fluorophenylmethyl)-fur-2-yl)-1-methyl-2-propenyl]-N-hydroxyurea, E-N-[3-(5-(4-Fluorophenylmethyl)-fur-2-yl)-1-methyl-2-propenyl]-N-hydroxyurea, Z-(R)-N-{3-[5-(4-fluorophenylmethyl)thiazo-2-yl]-1-methyl-2-propenyl}-N-hydroxyurea, E-(R)-N-{3-[5-(4-fluorophenylmethyl)thiazo-2-yl]-1-methyl-2-propenyl}-N-hydroxyurea, Z-(R)-N-[3-(5-(4-chlorophenylmethyl)-thien-2-yl)-1-methyl-2-propenyl]-N-hydroxyurea, Z-(R)-N-(3-(5-(3-pyridylmethyl)thien-2-yl)-1-methyl-2-propenyl)-N-hydroxyurea, Z-(R)-N-(3-(5-(4-pyridylmethyl)thien-2-yl)-1-methyl-2-propenyl)-N-hydroxyurea, Z-(R)-N-(3-(5-(2-pyridylmethyl)thien-2-yl)-1-methyl-2-propenyl)-N-hydroxyurea, Z-(R)-N-(3-(5-(thien-2-ylmethyl)thien-2-yl)-1-methyl-2-propenyl)-N-hydroxyurea, Z-(R)-N-(3-(5-(2-naphthylmethyl)thien-2-yl)-1-methyl-2-propenyl)-N-hydroxyurea, Z-(R)-N-(3-(5-(2-quinolylmethyl)thien-2-yl)-1-methyl-2-propenyl)-N-hydroxyurea, Z-(R)-N-(3-(5-(4-fluorophenylethyl)thien-2-yl)-1-methyl-2-propenyl)-N-hydroxyurea, Z-(R)-N-(3-(4-(4-fluorophenylmethyl)thien-2-yl)-1-methyl-2-propenyl)-N-hydroxyurea, Z-(R)-N-(3-(5-(4-biphenylmethyl)thien-2-yl)-1-methyl-2-propenyl)-N-hydroxyurea, Z-(R)-N-(3-(5-(thiazo-4-ylmethyl)thien-2-yl)-1-methyl-2-propenyl)-N-hydroxyurea, Z-(R)-N-(3-(5-(benzo[b]thien-2-ylmethyl)thien-2-yl)-1-methyl-2-propenyl)-N-hydroxyurea, Z-(R)-N-(3-(5-(thiazo-2-ylmethyl)thien-2-yl)-1-methyl-2-propenyl)-N-hydroxyurea, and Z-N-(3-(5-(4-fluorophenylmethyl)thien-2-yl)-2-propenyl)-N-hydroxyurea.

Preferred compounds of this invention are those in which Z is optionally substituted thienyl. Particularly preferred compounds are the E (trans)- and Z (cis)-(R)-N-(3-(5-(4-fluorophenylmethyl)-thien-2-yl)-1-methyl-2-propenyl)-N-hydroxyurea.

Leukotriene Biosynthesis Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 rain at 37° C. followed by calcium ionophore A23187 challenge (final concentration of 8.3 µM) and the reaction terminated after 30 minutes by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis in human whole blood. Representative results for specific examples are: $IC_{50}$=0.04 µM for Example 1 and $IC_{50}$=0.18 µM for Example 2.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at ambient temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the sell of the at to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e,g. two to four separate doses per day.

Preparation of Compounds of this Invention

The compounds of this invention can be prepared by a variety of synthetic routes. Representative procedures are outlined as follows.

Scheme 1a illustrates a general route for the preparation of the compounds of this invention involving the assembly of an heteroaryl template that can be functionalized to give the desired acetylenic N-hydroxyurea intermediate which is then reduced by known procedures of synthetic chemistry to provide either the Z (cis) alkene isomer or the E (trans) alkene isomer. The intermediate 2 (where Y1 and Y2 are selected from —O—, —S—, and —CH— is prepared by a coupling reaction of the two requisite intermediates shown in Scheme 1a. This reaction may be catalyzed by the addition of transition metal catalysts or their salts. The aryl moiety 2 is then converted to an aryl halide 3 or 4 which is then treated in a Pd catalyzed coupling reaction with an alkynyl-N-hydroxyurea, for example, butynyl-N-hydroxyurea, to provide the intermediate alkyne 5. Reduction of 5 by hydrogenation using a palladium catalyst in the presence of lead provides the Z (cis) alkene product 6. Reduction of 5 with diisobutylaluminum hydride provides the E (trans) alkene product 7.

Scheme 1a

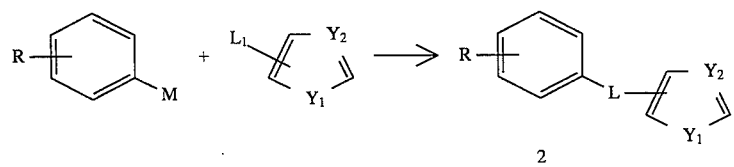

-continued
Scheme 1a

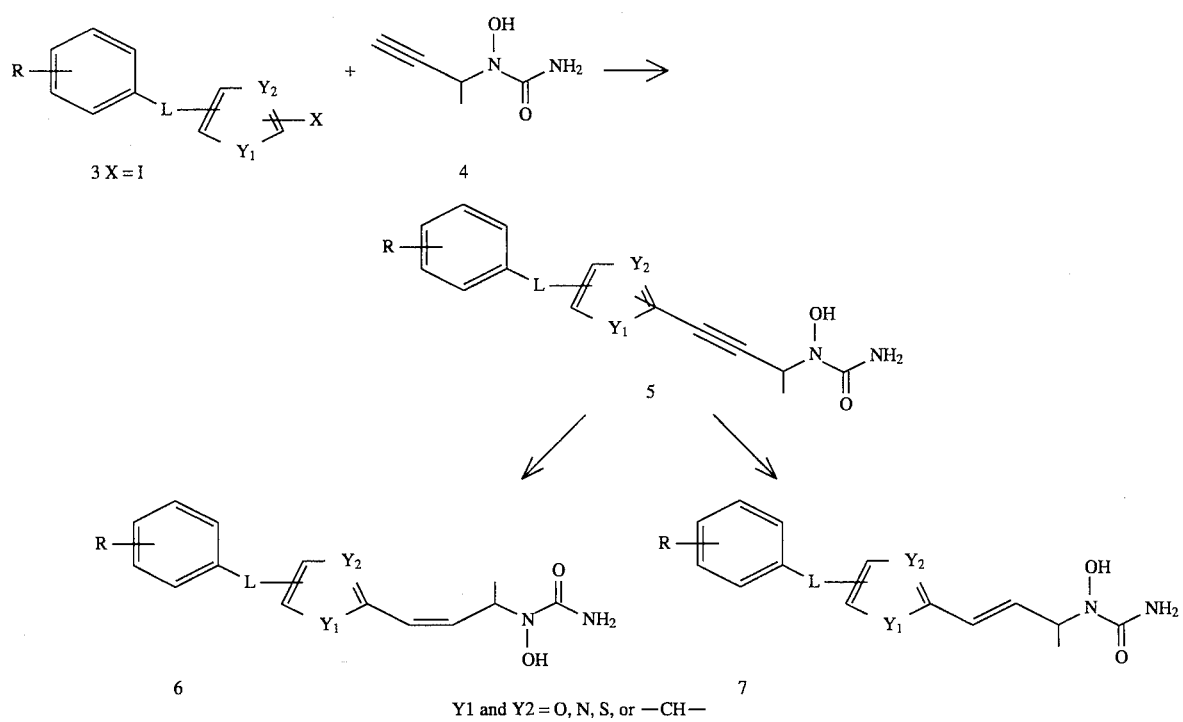

Y1 and Y2 = O, N, S, or —CH—

Scheme 1b illustrates an alternative route for the preparation of the acetylenic intermediates used in this invention. The intermediate 10 is prepared by coupling the two requisite intermediates 8 and 9 (where Y1 and Y2 is —O—, —N—, —S—, or —CH—). Hydrolysis of the diethylacetal provides the aldehyde 11, which is oxidized to the intermediate carboxylic acid 12 (for example using NaClO$_2$ in DMSO followed by NaH$_2$PO$_4$ in water). The carboxylic acid is converted into the iodo compound 123using NaOH, I$_2$, and KI. Intermediate 13 is then reacted by the procedures described in Scheme 1a with the 1-methyl-2-propynyl-N-hydroxyurea moiety to provide intermediate 5.

Also, the aryl aldehyde 11 (where Y1 and Y2 are —O—, —N—, —S—, or —CH—) is converted to the substituted butynol 14 by known methods (for example, treatment with carbon tetrabromide, triphenylphosphine and zinc, followed by lithium diisopropylamide and acetaldehyde). Alternatively aryl halide 13 can be converted to the butynol 14 by Pd catalyzed coupling with 3-hydroxybutyne as shown in Scheme 1c.

Scheme 1b

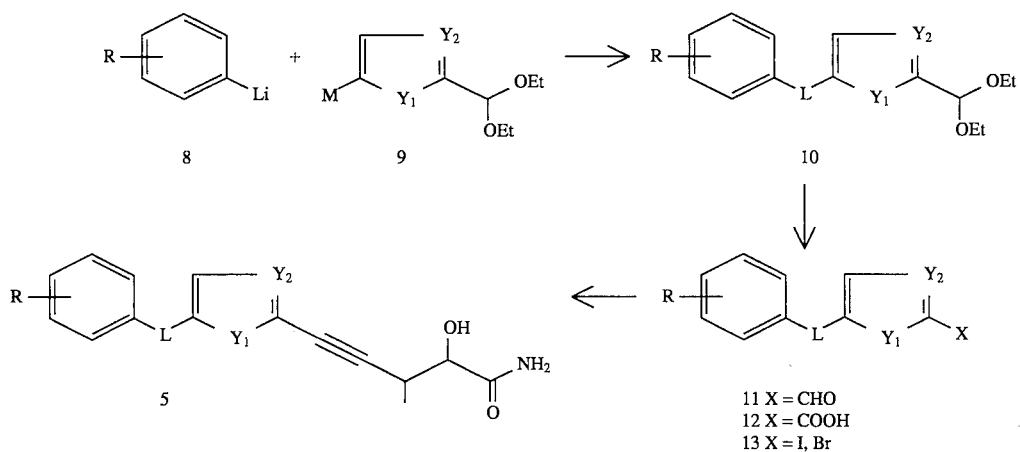

Scheme 1c

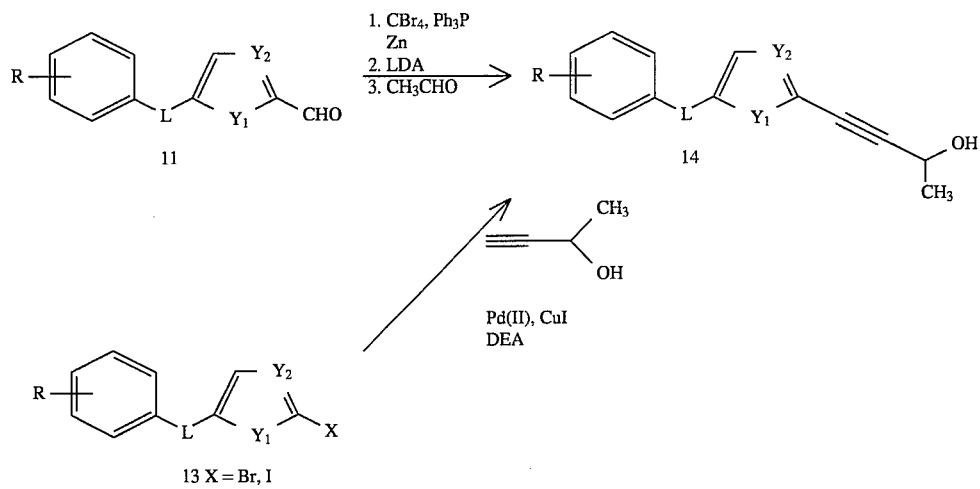

Another procedure is shown in Scheme 1d and involved the treatment of the substituted butynol 14 (where Y1 and Y2 are —O—, —N—, —S—, or —CH—) with triphenylphosphine, diethyl azodicarboxylate and N,O-bisphenoxycarbonylhydroxylamine followed by treatment with ammonia or ammonium hydroxide to provide the desired N-hydroxyureas 5 of this invention. Alternatively intermediate 13 can be coupled using a suitable palladium catalyst and the 1-methyl-2-propynyl-N-hydroxyurea 4 to give the intermediate 5.

deuterodimethylsulfoxide, DIBAL for diisobutylaluminum hydride.

Scheme 1d

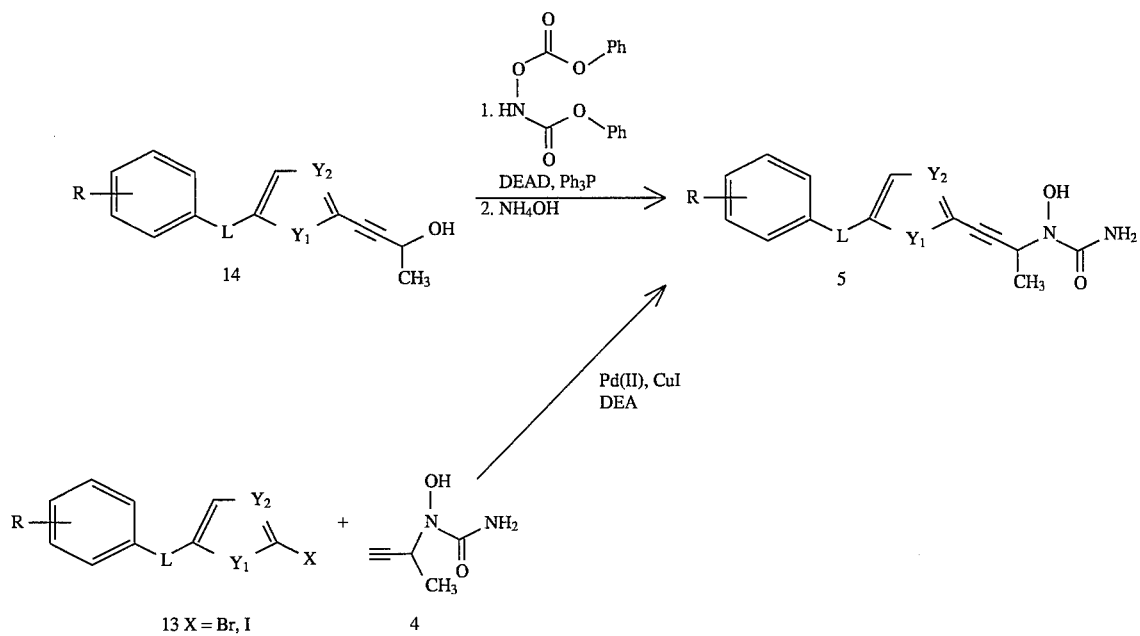

The foregoing may be better understood by reference to the following examples which are provided for illustration and not intended to limit the scope of the inventive concept. The following abbreviations are used: THF for tetrahydrofuran, n-BuLi for n-butyllithium, DMF for N,N-dimethylformamide, $CDCl_3$ for deuterochloroform, DMSO-$d_6$ for

EXAMPLE 1

Preparation of
Z-(R)-N-[3-(5-(4-Fluorophenylmethyl)-thien-2-yl)-1-methyl-2-propenyl] -N-hydroxyurea

Step 1: 2-(4-fluorophenylmethyl)thiophene

A solution of thiophene (12.6 g, 0.15 mol) in a mixture of anhydrous ether (230 mL) and anhydrous THF (70 mL) was treated dropwise at 0° C. with a 2.5M solution of n-butyllithium in hexane (54.0 mL, 0.134 mol). The mixture was stirred at 0° C. for 1.5 hours and then transferred by cannula into a −78° C. solution of 4-fluorobenzylbromide (23.6 g, 0.125 mol) containing tetrakis(triphenylphosphine) palladium(0) (1.25 g) in anhydrous THF (200 mL). The reaction mixture was stirred for 17 hours at ambient temperature and then quenched with saturated aqueous $NH_4Cl$ solution (100 mL) and partitioned between ether and additional $NH_4Cl$ solution. The ether layer was dried over $MgSO_4$, concentrated in vacuo and the residue subjected to vacuum distillation to give 19.4 g (81%) of 2-(4-fluorophenylmethyl)thiophene. b.p. 74°–83° C. at 0.6–0.7 mm of Hg.

Step 2: 2-iodo-5-(4-fluorophenylmethyl)thiophene

A mixture of 2-(4-fluorophenylmethyl)thiophene (3.85 g, 20.0 mmol), prepared as described in step 1, and N-iodosuccinimide (4.50 g, 20.0 mmol) in 1:1 chloroform-acetic acid (40 mL) was stirred at ambient temperature for 1 hour and then diluted with an equal volume of water. The organic layer was washed with saturated aqueous $NaHCO_3$ solution (2×50 mL), 10% aqueous sodium thiosulfate solution (2×50 mL) and once with brine. After drying over $MgSO_4$, the organic layer was concentrated in vacuo to give 6.07 g (95%) of 2-iodo-5-(4-fluorophenylmethyl)thiophene as a gold colored oil.

Step 3. (R)-N-hydroxy-N-(3-butyn-2-yl)urea

To a solution of (S)-O-p-toluenesulfonyl-3-butyn-2-ol (11.2 g, 50.0 mmol), prepared by addition of p-toluenesulfonyl chloride and triethylamine to (S)-3-butyn- 2-ol, in methanol (100 mL), was added 55% aqueous hydroxylamine (30 mL, 0.50 mol) and the reaction mixture was stirred at ambient temperature for 40 hours. The reaction mixture was cooled to 10° C. and concentrated HCl (50 mL) was added dropwise. The reaction mixture was concentrated in vacuo and the residue was partitioned between $H_2O$ (50 mL) and ethyl acetate (200 mL). The 2-phase mixture was cooled to 10° C. and taken to pH 8 with 50% aqueous NaOH solution (60 mL). After stirring for 15 min the layers were separated and the aqueous phase was extracted twice with 200 mL of ethyl acetate. The combined ethyl acetate extracts were cooled to 10° C. and a solution of KOCN (8.1 g, 0.10 mmol) in $H_2O$ (30 mL) was added, followed by dropwise addition of 11 mL of concentrated HCl, and the reaction mixture was stirred for 30 min. The ethyl acetate layer was separated and the aqueous layer was extracted twice with ethyl acetate. The combined organic layers were dried over $MgSO_4$, filtered, and concentrated in vacuo to give 5.9 g (92% yield) of (R)-N-hydroxy-N-(3-butyn-2-yl)urea. mp 129° C. $[\alpha]_D^{24}=+53.3°$ (c=0.58, $CH_3OH$). $^1H$ NMR (DMSO-$d_6$, 300 MHz) 67 1.25 (d, 3H, J=7 Hz), 3.05 (d, 1H, J=2.5 Hz), 4.85 (dq, 1H, J=2.5, 7 Hz), 6.50 (br s, 2H), 9.24 (s, 1H). $^{13}CNMR$ (DMSO-$d_6$, 75 MHz) δ18.43, 45.14, 72.81, 83.87, 161.51. IR (KBr) 3455, 3330, 3290, 3215, 1658, 1637, 1585 $cm^{-1}$. MS (DCI/$NH_3$) m/e 146 (M+$NH_4$)$^+$, 163 (M+$NH_4$.$NH_3$)$^+$. Anal. Calc for $C_5H_8N_2O_2$: C, 46.87; H, 6.29; N, 21.86. Found: C, 46.78; H, 6.34; N, 21.72.

Step 4.
(R)-N-{3-[5-(4-fluorophenylmethyl)thien-2-yl]-1-methyl-2-propynyl} -N-hydroxyurea To a solution of 2-iodo-5-(4-fluorophenylmethyl)thiophene (5.30 g, 16.6 mmol), prepared as in step 2, in anhydrous DMF (5.0 mL) was added (R)-N-hydroxy-N-(3-butyn-2-yl)urea (2.12 g, 16.6 mmol), triphenylphosphine (84 mg, 0.32 mmol), bis(acetonitrile)palladium(II) chloride (40 mg, 0.16 mmol), copper (I) iodide (16 rag, 0.08 mmol), and diethylamine (5.6 ml). The mixture was stirred under nitrogen at ambient temperature for 22 hours and concentrated in vacuo at 32 ° C. The residue was subjected to chromatography on silica eluting with 2–7% MeOH in $CH_2Cl_2$, crystallization from ethyl acetate-hexane and trituration in $CH_2Cl_2$ to afford (R)-N-{3-[5-(4-fluorophenylmethyl)thien-2-yl]-1-methyl-2-propynyl}-N-hydroxyurea as a cream-colored solid 0.94 g (18%). m.p. 135°–136° C.(dec). $^1H$ NMR (DMSO-$d_6$, 300 MHz) δ1.32 (d, J=6.0 Hz, 3H), 4.11 (s, 2H), 5.10 (q, J= 6.0Hz, 1H), 6.54 (s, 2H), 6.81 (d, J=3.0Hz, 1H), 7.08 (d, J=3.0Hz, 1H), 7.10– 7.18 (m, 2H), 7.25–7.32 (m, 2H), 9.33 (s, 1H). MS (DCI/$NH_3$) m/e 319 (M+H)$^+$. $[\alpha]_D^{23°}=+47.8°$ (C=1, MeOH). Anal calcd for $C_{16}H_{15}FN_2O_2S$: C, 60.36; H, 4.75; N, 8.80. Found: C, 60.31; H, 4.79; N, 8.50.

Step 5:
Z-(R)-N-[3-(5-(4-Fluorophenylmethyl)-thien-2-yl)-1-methyl-2-propenyl]-N-hydroxyurea A solution of (R)-N-{3-[5-(4-fluorophenylmethyl)thien-2-yl]-1-methyl-2-propynyl} -N-hydroxyurea (0.50 g, 1.57 mmol), prepared as in step 4, quinoline (0.25 mL, 2.11 mmol), and 5% palladium on calcium chloride poisoned with lead (0.025 g) in acetone (15 mL) was allowed to stir under hydrogen (atmospheric pressure) for 24 hours. The solution was filtered through celite and solvents removed in vacuo. The resulting oil was taken up in ethyl acetate (50mL) and washed with aqueous 1M $H_3PO_4$ (3×25 mL) and aqueous $NaHCO_3$ (3×25 mL). The solution was dried ($MgSO_4$) after which the solvent was evaporated to yield a yellow oil. The residue was purified by chromatography on silica gel (50% ethyl acetate/hexane/1% acetic acid). The resulting solid was crystallized from hot ethyl acetate/ hexane to yield 0.145g (29%) of Z-N-[3-(5-(4-Fluorophenylmethyl)-thien- 2-yl)-1-[R]-methyl-2-propenyl]-N-hydroxyurea. m.p. 123°–4° C., MS. (DCI/$NH_3$) m/e 321 (M+H)$^+$, 338 (M+$NH_4$)$^+$. $^1H$ NMR (DMSO-d6, 300 MHz) δ1.16 (d,J= 6.3 Hz, 3H), 4.1 (s, 2H), 5.25 (m, 1H), 5.67 (rid, J=9.0, 11.7 Hz, 1H), 6.35 (s, 2H), 6.43 (d, J=11.7 Hz, 1H), 6.83 (d, J=3.6 Hz, 1H), 6.94 (d, J=3.6 Hz, 1H), 7.13 (m, 2H), 7.32 (m, 2H), 9.18 (s, 1H). Anal calcd for $C_{17}H_{17}FN_2O_2S$: C, 59.98; H, 5.35; N, 8.74. Found C, 59.79; H, 5.25; N, 8.71.

EXAMPLE 2

Preparation of
E-(R)-N-[3-(5-(4-Fluorophenylmethyl)-thien-2-yl)-1-methyl-2-propenyl] -N-hydroxyurea To a solution of (R)-N-{3-[5-(4-fluorophenylmethyl)thien-2-yl]-1-methyl-2-propynyl} -N-hydroxyurea (0.316g, 1.05 mmol), prepared as in Example 1, step 4, in THF (8 mL) at −70° C. was added DIBAL (5.23 mL, 5.25 mmol). The reaction was slowly allowed to warm to ambient temperature over 17 hours. The reaction was quenched into an aqueous 1M H$_3$PO$_4$ solution and extracted with ethyl acetate. The combined organic layers were washed with aqueous NaHCO$_3$, dried (MgSO$_4$) and evaporated. The residue was purified by chromatography on silica gel (50% ethyl acetate/hexanes/1% acetic acid). The resulting solid was crystallized from hot ethyl acetate/hexanes to yield 0.063 g (20%) of E-N-[3-(5-(4-Fluorophenylmethyl)-thien-2-yl)-1-(R)-methyl-2-propenyl]-N-hydroxyurea. m.p. 143°–4° C). MS (DCI/NH$_3$) m/e 321 (M+H)$^+$, 338 (M+NH$_4$)$^+$. $^1$H NMR (DMSO-d6, 300 MHz) δ1.17(d, J=7.2 Hz, 3H), 4.08 (s, 2H), 4.73 (m, 1H), 5.88 (dd, J= 6.3, 15.6 Hz, 1H), 6.33 (s, 2H), 6.55 (d, J=15.6 Hz, 1H), 6.77 (d, J=4.2 Hz, 1H), 6.83 (d, J=4.2 Hz, 1H), 7.12 (m, 2H), 7.29 (m, 2H), 9.02 (s, 1H). Anal Calcd for C$_{17}$H$_{17}$FN$_2$O$_2$S: C, 59.98; H, 5.35; N, 8.74. Found C, 60.15; H, 5.11; N, 8.75.

EXAMPLE 3

Preparation of
Z-N-[3-(5-(4-Fluorophenylmethyl)-thien-2-yl)-1-methyl-2-propenyl] -N-hydroxyurea Step 1:
N,O-bis(phenoxycarbonyl)-N-(3-butyn-2-yl)-hydroxylamine To a 0° C. solution in THF (200 mL) of 3-butyn-2-ol (3.00 g, 42.9 mmol), N,O-bis(phenoxycarbonyl)hydroxylamine (11.7 g, 42.9 mmol), prepared according to the method of Stewart and Brooks, *J. Org. Chem.* 1992, 57, 5020, and triphenylphosphine (11.7 g, 42.9 mmol), was added dropwise diethylazodicarboxylate (7.40 g, 42.8 mmol). The reaction mixture was stirred for 2 hours at 0°–5° C. and then was concentrated almost to dryness. The residue was diluted with ethyl acetate, the solids were filtered off, and the filtrate was concentrated in vacuo. Chromatography on silica gel (5% ethyl acetate, pentane) provided N,O-bis(phenoxycarbonyl)-N-( 3-butyn-2-yl)hydroxylamine (12.3 g, 88%).

Step 2: N-(3-butyn-2-yl)N-hydroxyurea

A mixture of N,O-Bis(phenoxycarbonyl)-N-(3-butyn-2-yl)hydroxylamine (3.14 g,9.7 mmol), methanol (20 mL), and ammonium hydroxide (20 mL) was stirred for 17 hours at ambient temperature. The reaction mixture was concentrated in vacuo and the residue was dissolved in ethyl acetate. The organic solution was washed with brine, dried over MgSO$_4$, filtered, and concentrated. Chromatography on silica gel (2% methanol, methylene chloride) afforded N-(3-butyn-2-yl)N-hydroxyurea (340 rag, 28%). $^1$H NMR (DMSO-26, 300 MHz) δ1.25 (d, 3H, J= 7.5 Hz), 3.05 (d, 1H, J=3.0 Hz), 4.85 (dq, 1H, J=7.5, 3.0 Hz), 6.50 (br s, 1H), 9.25 (S, 1H). MS (DCI/NH$_3$) m/e 129 (M+H)$^+$, 146 (M+NH$_4$)$^+$. Anal calcd for C$_5$H$_8$N$_2$O$_2$: C, 46.87; H, 6.29; N, 21.86. Found: C, 47.03; H, 6.27; N, 21.98.

Step 3.
N-{3-[5-(4-fluorophenylmethyl)thien-2-yl]-1-methyl-2-propynyl}-N-hydroxyurea The desired compound is prepared according to the method of Example 1, step 4, except substituting N-(3-butyn-2-yl)N-hydroxyurea, prepared as in step 2, for (R)N-(3-butyn-2-yl)N-hydroxyurea.

Step 4:
Z-N-[3-(5-(4-Fluorophenylmethyl)-thien-2-yl)-1-methyl-2-propenyl]-N-hydroxyurea Racemic Z-N-[3-(5-(4-Fluorophenylmethyl)-thien-2-yl)-1-methyl-2-propenyl] -N-hydroxyurea is prepared according to the method of Example 1 ,step 5, except substituting N-{3-[5-(4-fluorophenylmethyl)-thien-2-yl]-1-methyl-2-propynyl} -N-hydroxyurea, prepared as in step 3, for (R) N-{3-[5-(4 -fluorophenylmethyl)-thien-2-yl]-1-methyl-2-propynyl}-N-hydroxyurea.

EXAMPLE 4

Preparation of
E-N-[3-(5-(4-Fluorophenylmethyl)-thien-2-yl)-1-methyl-2-propenyl] -N-hydroxyurea The desired compound is prepared according to the method of Example 2, except substituting N-{3-[5-(4-fluorophenylmethyl)-thien-2-yl]-1-methyl-2-propynyl} -N-hydroxyurea, prepared as in Example 3, step 2, for (R) N-{3-[5-(4 -fluorophenylmethyl)-thien-2-yl]-1-methyl-2-propynyl}-N-hydroxyurea.

EXAMPLE 5

Preparation of
Z-N-[3-(5-(4-Fluorophenylmethyl)-fur-2-yl)-1-methyl-2-propenyl]-N-hydroxyurea The desired compound is prepared according to the method of Example 1, except substituting furan for thiophene, and substituting N-(3-butyn-2-yl)N-hydroxyurea, prepared as in Example 3, step 2, for (R) N-(3-butyn-2-yl)N-hydroxyurea.

EXAMPLE 6

Preparation of
E-N-[3-(5-(4-Fluorophenylmethyl)-fur-2-yl)-1-methyl-2-propenyl]-N-hydroxyurea The desired compound is prepared according to the method of Example 2, except substituting furan for thiophene, and substituting N-(3-butyn-2-yl)N-hydroxyurea, prepared as in Example 3, step 2, for (R) N-(3-butyn-2-yl)N-hydroxyurea.

EXAMPLE 7

Preparation of
Z-(R)-N-{3-[5-(4-fluorophenylmethyl)thiazo-2-yl]-1-methyl-2-propenyl} -N-hydroxyurea The desired compound is prepared using the procedures described in Example 11, except substituting 5-(4-fluorophenylmethyl)thiazole for 2-(4-fluorophenylmethyl)thiophene.

EXAMPLE 8

Preparation of
E-(R)-N-{3-[5-(4-fluorophenylmethyl)thiazo-2-yl]-1-methyl-2 -propenyl}-N-hydroxyurea The desired compound is prepared according to the method of Example 2, except substituting (R)-N-{3-[5-(4-fluorophenylmethyl)thiazo-2-yl]-1-methyl-2-propynyl} -N-hydroxyurea, prepared as in Example 7, for (R)-N-{3-[5-(4 -fluorophenylmethyl)thien-2-yl]-1-methyl-2-propynyl}-N-hydroxyurea.

EXAMPLE 9

Preparation of
Z-(R)-N-[3-(5-(4-chlorophenylmethyl)-thien-2-yl)-1-methyl-2-propenyl]-N-hydroxyurea

Step 1: 4-chlorobenzyl bromide

To a suspension of 4-chlorobenzyl alcohol (14.26 g, 100 mmol) in $CH_2Cl_2$ (40 mL) at ambient temperature was added added dropwise a solution of $PBr_3$ in $CH_2Cl_2$ (1.0M, 32 mL, 32 mmol). The reaction mixture was stirred for 72 hours at ambient temperature and then was poured slowly onto ice. The layers were separated and the organic phase was dried over $MgSO_4$, filtered, and concentrated in vacuo to give 4-chlorobenzyl bromide (19.76 g) as a colorless solid.

Step 2: 2-(4-chlorophenylmethyl)thiophene

The desired compound was prepared according to the method of Example 1, step I, except substituting 4-chlorobenzyl bromide, prepared as in step 1, for 4-fluorobenzyl bromide, and using THF instead of the ether/THF mixture.

Step 3: 2-iodo-5-(4-chlorophenylmethyl)thiophene

The desired compound was prepared according to the method of Example 1, step 2, except substituting 2-(4-chlorophenylmethyl)thiophene for 2-(4-fluorophenylmethyl)thiophene.

Step 4:
(R)-N-{3-[5-(4-chlorophenylmethyl)thien-2-yl]-1-methyl-2-propynyl}-N-hydroxyurea The title compound was prepared using the procedures described in Example 1, step 4, except substituting 2-iodo-5-(4-chlorophenylmethyl)thiophene, prepared as in step 3, for 2-iodo-5-(4-fluorophenylmethyl)thiophene. mp 132°–13420 C. $^1$H NMR (DMSO-$d_6$) δ1.33 (d, J=7 Hz, 3H), 4.12 (s, 2H), 5.11 (q, J=7 Hz, 1H), 6.50 (bs, 2H), 6.82 (d, J=4 Hz, 1H), 7.08 (d, J=4 Hz, 1H), 7.28 (m, 2H), 7.37 (m, 2H), 9.30 (s, 1H). MS (DCI/$NH_3$) m/e 352 $(M+NH_4)^+$, 335 $(M+H)^+$, 259. Anal calcd for $C_{16}H_{15}N_2O_2S$: C, 57.40; H, 4.52; N, 8.37. Found: C, 57.46; H, 4.26; N, 8.40.

Step 5:
Z-(R)-N-[3-(5-(4-chlorophenylmethyl)-thien-2-yl)-1-methyl-2-propenyl]-N-hydroxyurea The desired compound is prepared according to the method of Example 1, step 5, except substituting (R)-N-{3-[5-(4-chlorophenylmethyl)thien-2-yl]-1-methyl-2-propynyl}-N-hydroxyurea, prepared as in step 4, for (R)-N-{3-[5-(4-fluorophenylmethyl)thien-2-yl]-1-methyl-2-propynyl}-N-hydroxyurea.

EXAMPLE 10

Preparation of
Z-(R)-N-(3-(5-(3-pyridylmethyl)thien-2-yl)-1-methyl-2-propenyl)-N-hydroxyurea

Step 1: 2-(3-pyridylhydroxymethyl)thiophene

To a solution of 3-pyridinecarboxaldehyde (5.0 mL, 53 mmol) in THF at −78° C. was added 2-thienyllithium (1.0M in THF, 64 mL, 64 mmol) and the reaction mixture was stirred for 2 hours at −78° C. The reaction mixture was quenched with saturated aqueous $NH_4Cl$ and extracted with ether. The organic phase was dried over $MgSO_4$, filtered, and concentrated in vacuo. Chromatography on silica gel (5%, then 10% methanol/$CHCl_3$) gave 2-(3-pyridylhydroxymethyl)thiophene (6.30 g, 62% yield).

Step 2: 2-(3-pyridylmethyl)thiophene

To a solution of 2-(3-pyridylhydroxymethyl)thiophene (8.82 g, 46.2 mmol), prepared as in step 1, in acetic acid (50 mL) was added tin(H)chloride dihydrate (22.9 g, 101 mmol) and HCl gas was bubbled through the reaction mixture for about 10 min. The reaction mixture was stirred for 1.5 hours at ambient temperature, and the liquid was decanted, concentrated in vacuo to a volume of about 10 mL, and poured into $H_2O$. The aqueous solution was made basic by the slow addition of saturated aqueous $NaHCO_3$ and extracted with ethyl acetate/ether. The organic phase was dried over $MgSO_4$, filtered, and concentrated in vacuo. Chromatography on silica gel (5% methanol/$CHCl_3$) gave 2-(3-pyridylmethyl)thiophene (2.63 g).

Step 3:
Z-(R)-N-(3-(5-(3-pyridylmethyl)thien-2-yl)-1-methyl-2-propenyl)-N-hydroxyurea The desired compound is prepared according to the method of Example 1, steps 2–5, except substituting 2-(3-pyridylmethyl)thiophene, prepared as in step 2, for 2-(4-fluorophenylmethyl)thiophene.

EXAMPLE 11

Preparation of
Z-(R)-N-(3-(5-(4-pyridylmethyl)thien-2-yl)-1-methyl-2-propenyl)-N-hydroxyurea

Step 1:
2-iodo-5-(4-pyridylhydroxymethyl)thiophene

To a solution of LDA (11 mmol) in THF at −78° C. was added 2-iodothiophene (2.1 g, 10 mmol). After stirring for 0.5 hours at −78° C., a solution of 4-pyridinecarboxaldehyde (1.07 g, 10 mmol) in THF (10 mL) was added dropwise and the reaction mixture was warmed slowly to ambient temperature and stirred for 16 hours. The reaction was quenched with saturated aqueous $NH_4Cl$, diluted with $H_2O$, and extracted twice with ethyl acetate. The combined organic layers were dried over $MgSO_4$, filtered, and concentrated in vacuo. Chromatography on silica gel (80% ethyl acetate/hexanes) provided 2-iodo-5-(4-pyridiylhydroxymethyl)thiophene (1.39 g, 40% yield) as a tan solid.

Step 2: 2-iodo-5-(4-pyridylmethyl)thiophene

A suspension of 2-iodo-5-(4-pyridylhydroxymethyl)thiophene (0.65 g, 2.05 mmol) and tin(II) chloride dihydrate (1.01 g, 4.51 mmol) in acetic acid (5 mL) was treated with HCl gas for 10 rain and stirred for 2 hours at ambient temperature. The reaction mixture was poured into $H_2O$, neutralized with 10% aqueous NaOH, and extracted twice with ethyl acetate. The combined organic layers were washed with $H_2O$, dried over $MgSO_4$, filtered, and concentrated in vacuo. Chromatography on silica gel provided 2-iodo-5-(4-pyridylmethyl)thiophene (0.22 g, 36% yield) as a white solid.

Step 3:
Z-(R)-N-(3-(5-(4-pyridylmethyl)thien-2-yl)-1-methyl-2-propenyl)-N-hydroxyurea The desired compound is prepared according to the method of Example 1, steps 4 and 5, except substituting 2-iodo-5-(4-pyridylmethyl)thiophene, prepared as in step 2, for 2-iodo-5-(4-fluorophenylmethyl)thiophene.

EXAMPLE 12

Preparation of
Z-(R)-N-(3-(5.-(2-pyridylmethyl)thien-2-yl)-1-methyl-2-propenyl)-N-hydroxyurea The desired compound is prepared according to the method of Example 10, except substituting 2-pyridinecarboxaldehyde for 3-pyrdinecarboxaldehyde.

EXAMPLE 13

Preparation of
Z-(R)-N-(3-(5-(thien-2-ylmethyl)thien-2-yl)-1-methyl-2-propenyl)-N-hydroxyurea The desired compound is prepared according to the method of Example 1, steps 2–5, except substituting 2-(thien-2-ylmethyl)thiophene for 2-(4-fluorophenylmethyl)thiophene.

EXAMPLE 14

Preparation of
Z-(R)-N-(3-(5-(2-naphthylmethyl)thien-2-yl)-1-methyl-2-propenyl)-N-hydroxyurea Step 1: 2-iodo-5-(2-naphthylmethyl)thiophene The desired compound was prepared according to the method of Example 11, step 1, except substituting 2-(bromomethyl)naphthylene for 4-pyridinecarboxaldehyde.

Step 2:
Z-(R)-N-(3-(5-(2-naphthylmethyl)thien-2-yl)-1-methyl-2-propenyl)-N-hydroxyurea The desired compound is prepared according to the method of Example 1, steps 4 and 5, except substituting 2-iodo-5-(2-naphthylmethyl)thiophene, prepared as in step 1, for 2-iodo-5-(4-fluorophenylmethyl)thiophene.

EXAMPLE 15

Preparation of
Z-(R)-N-(3-(5-(2,quinolylmethyl)thien-2-yl)-1-methyl-2-propenyl)-N-hydroxyurea The desired compound is prepared according to the method of Example 11, except substituting 2-quinolinecarboxaldehyde for 4-pyridinecarboxaldehyde.

EXAMPLE 16

Preparation of
Z-(R)-N-(3-(5-(4-fluorophenylethyl)thien-2-yl)-1-methyl-2-propenyl)-N-hydroxyurea The desired compound is prepared according to the method of Example 9, except substituting 4-fluorophenethyl alcohol for 4-chlorobenzyl alcohol.

EXAMPLE 17

Preparation of
Z-(R)-N-(3-(4-(4-fluorophenylmethyl)thien-2-yl)-1-methyl-2-propenyl)-N-hydroxyurea Step 1: 2-iodo-4-(4-fluorophenylmethyl)thiophene To a solution of LDA (3.67 mmol) in THF at −78° C. was added a solution of 3-(4-fluorophenylmethyl)thiophene (640 rag, 3.33 mmol), prepared as in Example 35, step 1, and the reaction mixture was stirred for 25 min. A solution of $I_2$ (1.01 g, 4.00 mmol) in THF was added and the cold bath was removed. The reaction mixture was warmed to ambient temperature, quenched with saturated aqueous $NH_4Cl$, and extracted with ether. The organic phase was washed with 1N aqueous $H_3PO_4$, saturated aqueous $NaHCO_3$, saturated aqueous $Na_2S_2O_3$, and brine, dried over $MgSO_4$, filtered, and concentrated in vacuo to give 928 mg of 2-iodo-4-(4-fluorophenylmethyl)thiophene which was used without further purification.

Step 2:Z-(R)-N-(3-(4-(4-fluorophenylmethyl)thien-2-yl)-1-methyl-2-propenyl)-N-hydroxyurea The desired compound is prepared according to the method of Example 1, steps 4 and 5, except substituting 2-iodo-4-(4-fluorophenylmethyl)thiophene, prepared as in step 1, for 2-iodo-5-(4-fluorophenylmethyl)thiophene.

EXAMPLE 18

Preparation of
Z-(R)-N-(3-(5-(4-biphenylmethyl)thien-2-yl)-1-methyl-2-propenyl)-N-hydroxyurea Step 1:
2-iodo-5-(4-biphenylhydroxymethyl)thiophene The desired compound was prepared according to the method of Example 11, step 1, except substituting 4-biphenylcarboxaldehyde for 4-pyridinecarboxaldehyde.

Step 2: 2-iodo-5-(4-biphenylmethyl)thiophene

To a solution of 2-iodo-5-(4-biphenylhydroxymethyl)thiophene (1.96 g, 5.0 mmol), prepared as in step 1, in dichloroethane (30 mL), was added sodium cyanoborohydride (2.2 g, 35 mmol), and $ZnI_2$ (2.0 g, 6.3 mmol). The reaction mixture was stirred for 6 hours at ambient temperature and then was filtered through a pad of celite. The filter cake was rinsed with $CH_2Cl_2$ and hexane, and the filtrate was concentrated in vacuo. Pure 2-iodo-5-(4-biphenylmethyl)thiophene (1.7 g) was obtained by chromatography on silica gel (3% ethyl acetate/hexane) and recrystallization from hexane/ethyl acetate.

Step 3:
Z-(R)-N-(3-(5-(4-biphenylmethyl)thien-2-yl)-1-methyl-2-propenyl)-N-hydroxyurea The desired compound is prepared according to the method of Example 1, steps 4 and 5, except substituting 2-iodo-5-(4-biphenylmethyl)thiophene, prepared as in step 2, for 2-iodo-5-(4-fluorophenylmethyl)thiophene.

EXAMPLE 19

Preparation of
Z-(R)-N-(3-(5-(thiazol-4-ylmethyl)thien-2-yl)-1-methyl-2-propenyl)-N-hydroxyurea

Step 1: 2-(thiazo-4-ylmethyl)thiophene

To a suspension of 4-chloromethylthiazole hydrochloride (3.41 g, 20.0 mmol) in THF (50 mL) was added triethylamine (3.04 g, 30.0 mmol) in one portion and the suspension was stirred for 2 hours at ambient temperature. The solid was then filtered off and rinsed with THF. The combined filtrate and washings were cooled to −78° C. and a solution of 2-thienyllithium in THF (20.0 mmol), prepared as in Example 12, step 1, was added over 10 min. The reaction mixture was stirred for 1 hour at −78° C. and then 17 hours at ambient temperature. The reaction was quenched with saturated aqueous $NH_4Cl$ and diluted with ether. The organic phase was separated, dried over $MgSO_4$, filtered, and concentrated in vacuo to give a maroon-colored oil. Chromatography on silica gel provided 2-(thiazo-4-ylmethyl)thiophene (0.325 g).

Step 2: Z-(R)-N-(3-(5-(thiazo-4-ylmethyl)thien-2-yl)-1-methyl-2-propenyl)-N-hydroxyurea The desired compound is prepared according to the method of Example 1, steps 2–5, except substituting 2-(thiazo-4-ylmethyl)thiophene, prepared as in step 1, for 2-(4-fluorophenylmethyl)thiophene.

EXAMPLE 20

Preparation of
Z-(R)-N-(3-(5-(benzo[b]thien-2-ylmethyl)thien-2-yl)-1-methyl-2-propenyl)-N-hydroxyurea The desired compound is prepared according to the method of Example 18, except substituting benzo[b]thiophene-2-carboxaldehyde for 4-biphenycarboxaldehyde.

EXAMPLE 21

Preparation of
Z-(R)-N-(3-(5-(thiazo-2-ylmethyl)thien-2-yl)-1-methyl-2-propenyl)-N-hydroxyurea

Step 1: 2-thiopheneacetamide

To a mixture of concentrated $NH_4OH$ (100 mL) and ice was added 2-thiopheneacetyl chloride (13.0 g, 80.9 mmol). The desired compound crystallized from the reaction mixture. Recrystallization from hot water gave 2-thiopheneacetamide (8.08 g, 64% yield) as white crystals. mp 146°–147° C.

Step 2: 2-thiophenethioacetamide

To a solution in THF (20(3 mL) of 2-thiopheneacetamide (4.04 g, 28.6 mmol), prepared as in step 1, was added $P_4S_{10}$ (12,7 g, 28.6 mmol), and the vigorously stirred reaction mixture was placed in a Bransonic 221 bath and sonicated with ultrasound for 30 min. The reaction mixture was filtered and the filtrate was concentrated in vacuo. The crude product was taken up in $CH_2Cl_2$ and decanted from the solid residue. Pure 2-thiophenethioacetamide (2.45 g, 54% yield) was obtained by chromatography on silica gel ($CH_2Cl_2$).

Step 3: 2-(thiazo-2-ylmethyl)thiophene

A solution of 2-thiophenethioacetamide (3.35 g, 21.3 mmol) in benzene (125 mL) was heated at reflux while 50% aqueous chloroacetaldehyde (6.62 g, 42.0 mmol) was added dropwise. The reaction mixture was heated for 2.5 hours at reflux, then left standing at −20° C. for 17 hours. After warming to reflux and heating for another hour, the reaction mixture was cooled to ambient temperature and the layers were separated. The organic layer was concentrated in vacuo to give 3.08 g of a dark oil. Chromatography on silica gel ($CH_2Cl_2$) gave 2-(thiazo-2-ylmethyl)thiophene (1.24 g). The aqueous phase was treated with decolorizing carbon and filtered. The filtrate was taken to pH 11 with 6N aqueous NaOH and extracted twice with ether. The combined ether layers were dried over KOH, filtered, and concentrated in vacuo to to give an additional 1.02 g of 2-(thiazo-2-ylmethyl)thiophene (total yield 2.26 g, 58%).

Step 4: Z-(R)-N-(3-(5-(thiazo-2-ylmethyl)thien-2-yl)-1-methyl-2-propenyl)-N-hydroxyurea The desired compound is prepared according to the method of Example 1, steps 2–5, except substituting 2-(thiazo-2-ylmethyl)thiophene, prepared as in step 3, for 2-(4-fluorophenylmethyl)thiophene.

EXAMPLE 22

Preparation of
Z-N-(3-(5-(4-fluorophenylmethyl)thien-2-yl)-2-propenyl)-N-hydroxyurea The desired compound is prepared according to the method of Example 3, except substituting propargyl alcohol for 3-butyn-2-ol.

We claim:
1. A compound of the formula

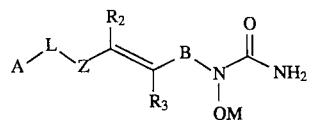

or a pharmaceutically acceptable salt thereof wherein

M represents hydrogen, or a pharmaceutically acceptable cation;

B is a straight or branched divalent alkylene group of one to twelve carbon atoms:

Z is selected from the group consisting of
  a) thienyl, optionally substituted with alkyl of one to six carbon atoms, or haloalkyl of one to six carbon atoms, and
  b) furyl, optionally substituted with alkyl of one to six carbon atoms, or haloalkyl of one to six carbon atoms:

L is alkylene of one to six carbon atoms:

A is optionally substituted phenyl wherein the optional substituents on the phenyl group are selected from the group consisting of
  alkyl of one to six carbon atoms,
  haloalkyl of one to six carbon atoms,
  hydroxyalkyl of one to six carbon atoms,
  alkoxy of one to twelve carbon atoms,
  alkoxyalkoxyl in which the two alkoxy portions may each independently contain one to six carbon atoms, alkylthio of one to six carbon atoms,
hydroxy,
halogen,
cyano,
amino,
alkylamino of one to six carbon atoms,
dialkylamino in which the two alkyl groups may independently contain one to six carbon atoms,
alkanoylamino of two to eight carbon atoms,
N-alkanoyl-N-alkylamino in which the alkanoyl portion may contain from two to eight carbon atoms and the alkyl groups may each independently contain one to six carbon atoms,
alkylaminocarbonyl of two to eight carbon atoms,
dialkylaminocarbonyl in which the two alkyl groups may independently contain one to six carbon atoms,
carboxyl, and
alkoxycarbonyl of two to eight carbon atoms, and
$R^2$ and $R^3$ are hydrogen.

2. A compound or pharmaceutically acceptable salt thereof as defined by claim 1 wherein Z is selected from the group consisting of unsubstituted furyl and furyl substituted with one or more substituents selected from the group consisting of alkyl of one to six carbon atoms, and haloalkyl of one to six carbon atom.

3. A compound or pharmaceutically acceptable salt thereof as defined by claim 1 wherein Z is selected from the group consisting of unsubstituted thienyl and thienyl substituted with one or more substituents selected from the group consisting of alkyl of one to six carbon atoms, and haloalkyl of one to six carbon atom.

4. A compound or pharmaceutically acceptable salt thereof as defined by claim 1 selected from the group consisting of:
Z-(R)-N-(3-(5-(4-fluorophenylmethyl)-thien-2-yl)-1-methyl-2-propenyl)-N-hydroxyurea,
E-(R)-N-(3-(3-(4-fluorophenylmethyl)-thien-2-yl)-1-methyl-2-propenyl)-N-hydroxyurea,
Z-N-(3-(5-(4-fluorophenylmethyl)-thien-2-yl)-1-methyl-2-propenyl)-N-hydroxyurea,
E-N-(3-(5-(4-fluorophenylmethyl)-thien-2-yl)-1-methyl-2-propenyl)-N-hydroxyurea,
Z-N-(3-(5-(4-fluorophenylmethyl)-fur-2-yl)-1-methyl-2-propenyl)-N-hydroxyurea,
E-N-(3-(5-(4-fluorophenylmethyl)-fur-2-yl)-1-methyl-2-propenyl)-N-hydroxyurea,
Z-(R)-N-(3-(5-(4-chlorophenylmethyl)-thien-2-yl)-1-methyl-2-propenyl)-N-hydroxyurea,
Z-(R)-N-(3-(5-(3-pyridylmethyl)thien-2-yl)-1-methyl-2-propenyl)-N-hydroxyurea,
Z-(R)-N-(3-(5-(thien-2-ylmethyl)thien-2-yl)-1-methyl-2-propenyl)-N-hydroxyurea,
Z-(R)-N-(3-(5-(4-fluorophenylethyl)thien-2-yl)-1-methyl-2-propenyl)-N-hydroxyurea,
Z-(R)-N-(3-(4-(4-fluorophenylmethyl)thien-2-yl)-1-methyl-2-propenyl)-N-hydroxyurea, and
Z-N-(3-(5-(4-fluorophenylmethyl)thien-2-yl)-2-propenyl)-N-hydroxyurea.

5. A compound or pharmaceutically acceptable salt thereof as defined by claim 1 selected from the group consisting of
E-(R)-N-[3-(5-(4-fluorophenylmethyl)-thien-2-yl)-1-methyl-2-propenyl]-N-hydroxyurea, and
Z-(R)-N-[3-(5-(4-fluorophenylmethyl)-thien-2-yl)-1-methyl-2-propenyl]-N-hydroxyurea.

6. A method for inhibiting lipoxygenase activity or leukotriene biosynthesis in a mammal in need of such treatment, comprising administering to the mammal a therapeutically effective amount of a compound of claim 1.

7. An composition for inhibiting lipoxygenase activity or the biosynthesis of leukotrienes comprising a pharmaceutically acceptable carrier and a therapeutically effective amount of a compound of claim 1.

* * * * *

UNITED STATES PATENT AND TRADEMARK OFFICE
CERTIFICATE OF CORRECTION

Page 1 of 2

PATENT NO. : 5,506,261
DATED : April 9, 1996
INVENTOR(S) : Dee W. Brooks, et al.

It is certified that error appears in the above-indentified patent and that said Letters Patent is hereby corrected as shown below:

Column 10, Line 21, change "sell" to --skill--.

Column 10, Line 21, change "at" to --art--.

Column 15, Line 63, change "67" to --$\delta$--.

Column 16, Line 1, change "$NH_4.NH_3$" to --$NH_4 \cdot NH$--.

Column 16, Line 51, change "rid" to --dd--.

Column 19, Line 39, change "13420" to --134°--.

Column 20, Line 11, change "(H)" to --(II)--.

Column 20, Line 60, change "rain" to --min--.

Column 21, Line 12, change "(5." to --(5--.

Column 22, Line 11, change "rag" to --mg--.

UNITED STATES PATENT AND TRADEMARK OFFICE
CERTIFICATE OF CORRECTION

PATENT NO. : 5,506,261
DATED : April 9, 1996
INVENTOR(S) : Dee W. Brooks, *et al.*

It is certified that error appears in the above-indentified patent and that said Letters Patent is hereby corrected as shown below:

Column 23, Line 59, change "(20(3mL)" to --(200mL)--.

Column 25, Line 37, change "(3-(3-(4-" to --(3-(5-(4-    --.

Signed and Sealed this

Twenty-second Day of October, 1996

Attest:

BRUCE LEHMAN

*Attesting Officer*    *Commissioner of Patents and Trademarks*